(12) United States Patent
Foland

(10) Patent No.: US 7,809,104 B2
(45) Date of Patent: Oct. 5, 2010

(54) IMAGING SYSTEM WITH LONG-STANDOFF CAPABILITY

(75) Inventor: Andrew D. Foland, Cambridge, MA (US)

(73) Assignee: L-3 Communications Security and Detection Systems Inc., Woburn, MA (US)

(*) Notice: Subject to any disclaimer, the term of this patent is extended or adjusted under 35 U.S.C. 154(b) by 88 days.

(21) Appl. No.: 11/599,018

(22) Filed: Nov. 13, 2006

(65) Prior Publication Data

US 2007/0140423 A1   Jun. 21, 2007

Related U.S. Application Data

(60) Provisional application No. 60/735,674, filed on Nov. 11, 2005.

(51) Int. Cl.
*G01N 23/04* (2006.01)
(52) U.S. Cl. .............................. 378/57; 378/86; 378/87; 378/88; 378/198
(58) Field of Classification Search .................. 378/57, 378/86–88, 198
See application file for complete search history.

(56) References Cited

U.S. PATENT DOCUMENTS

| | | | | | |
|---|---|---|---|---|---|
| 4,975,917 | A | * | 12/1990 | Villa | 372/5 |
| 5,224,144 | A | * | 6/1993 | Annis | 378/146 |
| 5,548,630 | A | * | 8/1996 | Hell et al. | 378/137 |
| 5,602,894 | A | * | 2/1997 | Bardash | 378/87 |
| 5,763,903 | A | * | 6/1998 | Mandai et al. | 257/186 |
| 5,764,683 | A | * | 6/1998 | Swift et al. | 378/57 |
| 6,081,580 | A |  | 6/2000 | Grodzins et al. | |
| 6,125,165 | A | * | 9/2000 | Warburton et al. | 378/86 |
| 6,421,420 | B1 |  | 7/2002 | Grodzins et al. | |
| 6,542,580 | B1 | * | 4/2003 | Carver et al. | 378/57 |
| 6,605,473 | B1 | * | 8/2003 | Hajduk et al. | 436/174 |
| 7,151,447 | B1 | * | 12/2006 | Willms et al. | 340/540 |

(Continued)

FOREIGN PATENT DOCUMENTS

WO    WO 2005121756 A2 * 12/2005

OTHER PUBLICATIONS

Kuyumchyan et al. "Study of optical properties of x-ray system based on two zone plates" IMT RAS Chernogolovka, Moskow District, Russia; Jul. 2005; 5 pages.

(Continued)

*Primary Examiner*—Edward J Glick
*Assistant Examiner*—Mona M Sanei
(74) *Attorney, Agent, or Firm*—Wolf, Greenfield & Sacks, P.C.

(57) ABSTRACT

An imaging system that can form an image of an item under inspection using scattered radiation. A pencil beam of radiation is steered over the item under inspection and scattered radiation is detected. Regions of the item under inspection from which radiation is scattered are resolved in three dimensions using two-dimensional coordinates to which the pencil beam is steered. The third dimension is resolved using time of flight from the source. Because the inspection system can be located on one side of an item under inspection, an item may be imaged from a long distance and the imaging system may be mounted on a moving vehicle, making the imaging system well suited for use in many security inspection systems to detect explosives and other contraband items.

26 Claims, 8 Drawing Sheets

U.S. PATENT DOCUMENTS

2004/0086078 A1* 5/2004 Adams et al. .................. 378/57
2005/0226383 A1* 10/2005 Rifkin et al. ................. 378/119
2006/0176998 A1* 8/2006 Korsunsky ................... 378/71

OTHER PUBLICATIONS

Baron "A Refractive Collimator for Synchrotron Radiation" Spring-8 Instrumentation & Techniques; 1999; pp. 51-52.

Pereira et al. "Parabolic lithium refractive optics for x-rays" Review of Scientific Instruments, Jan. 2004, pp. 37-41; vol. 75.

Forth "Design and Fabrication of Compound Refractive X-ray Lenses for CHESS" Dept. of Physics, Oberlin College, Ohio; 2000; pp. 1-9.

Pereira et al. "Lithium X-ray Refractive Lenses" Dept. of Physics, University of Michigan, Dec. 2002; 2 pages.

Pereira et al. "Large Aperture X-ray refractive Lens from Lithium" Dept. of Physics, University of Michigan; Nov. 2004; pp. 174-184; vol. 5539.

Search Report from International Application No. PCT/US2006/044195 dated Jan. 8, 2008, 7 pages.

* cited by examiner

IMAGING SYSTEM WITH LONG-STANDOFF CAPABILITY

CROSS-REFERENCE TO RELATED APPLICATIONS

This Application is a Non-Provisional of Provisional (35 USC 119(e)) application 60/735,674 entitled "IMAGING DEVICE USING ELECTROMAGNETICALLY-CONTROLLED FOCUSED X-RAY BACKSCATTER BEAM WITH LONGITUDINAL MEASUREMENT SYSTEM FOR LONG-STANDOFF CAPABILITY," filed on Nov. 11, 2005, and hereby incorporated by reference in its entirety.

BACKGROUND OF THE INVENTION

1. Field of the Invention

This invention relates generally to x-ray imaging systems and more specifically to security inspection systems.

2. Description of Related Art

Systems that can form an image of an item are used in a variety of applications. Many such systems construct images using information acquired from the interaction of penetrating radiation with an item under inspection. Different systems may be constructed to gather information following different types of interactions. For example, transmission systems illuminate an item with penetrating radiation, such as x-rays, and measure the radiation after it has passed through the item. By computing the attenuation of the radiation as it passed through the item, information about objects within the item can be determined and can be used to form an image of the item, including objects within it.

Other systems acquire information on an item by measuring radiation that has been scattered by the item. For example, an inspection system may illuminate a first column of an item with penetrating radiation and measure radiation emanating from the item in a second column. These columns are positioned to intersect at a region and the measured radiation represents radiation scattered from the region as a result of interaction between the incident beam and material in this region. Because the amount of scattering depends on material characteristics, the measured radiation can be used as an indication of the type of material in that region.

These systems obtain information about objects that are inside an item and therefore hidden from direct observation. This capability has led to use of imaging systems in security inspection systems. In a security inspection system, information obtained with the imaging system is analyzed to identify contraband objects within an item under inspection without the need to physically open the item.

Multiple analysis approaches are used. Some security inspection systems render information on a visual display for analysis by a human operator who is trained to recognize images of contraband items. In other systems, an image is processed by a computer that can detect a pattern of values that is characteristic of a contraband item. For example, a gun, knife or other metal object that could be used as a weapon interacts with radiation very differently than clothes or other items commonly found in a suitcase. Accordingly, an image of an item may contain a pattern of values that can be recognized as a weapon. Other contraband items, such as explosives, may similarly produce a pattern in an image that is sufficiently distinctive to allow those contraband items to be detected upon analysis of an image formed using penetrating radiation.

The ease with which contraband can be detected with security inspection system has led to widespread use of such systems in the airline travel industry. However, security inspection systems are used in other settings. Systems that can inspect cargo containers and other packages also are in use. Some of these systems are mounted on trucks and other vehicles so that they can be moved to inspect large stationary objects.

BRIEF SUMMARY OF THE INVENTION

In one aspect, the invention relates to a method of imaging an item. According to the method, an x-ray beam is scanned over the item. The intensity and scattering time of radiation scattered from the item is measured and an image of the item is formed based at least in part on the measured intensity and scattering time.

In another aspect, the invention relates to an inspection system comprising a steerable source adapted to emit a collimated beam of radiation toward an illumination area. The collimated beam has a narrow beam width at a distance in excess of 50 meters. A detector panel is positioned to receive radiation from the direction of the illumination area. A data analysis system forms an image of an item proximate the illumination area. The image has a plurality of regions, each region having a value based on the magnitude of an output of the detector panel at a time relative to the time at which the collimated beam of radiation was emitted toward the illumination area.

DETAILED DESCRIPTION

An improved inspection system may be constructed by capturing scattered radiation caused by interaction of a narrow beam of radiation with an item under inspection. Because the beam is narrow, captured scattered radiation can be correlated with a small region of an item that is irradiated with the beam. The region can be resolved in two dimensions based on the direction in which the beam is focused. Information on individual voxels can be obtained by resolving captured radiation in a third dimension based on time of flight. Because the regions are small, the resulting image has sufficient resolution to detect contraband.

By scanning the beam across the item under inspection and capturing data at numerous points, a three dimensional image of the item under inspection can be formed. This image can be analyzed to detect groups of voxels that depict suspicious regions in the item. This analysis may be performed by a computer, by rendering the image for a human to view or by a combination of computer and human processing. However, any suitable form of analysis may be used.

Because such a system can be implemented with all components on one side of an item under inspection, the system can be used to inspect items at a relatively large distance from the inspection system. In some embodiments, this "stand-off" may be in excess of 50 meters. Some embodiments may be designed for imaging objects at a distance of approximately 70 to 80 meters. However, the stand-off is not a limitation on the invention and a system may be constructed to operate at any suitable range.

Figure 1A:
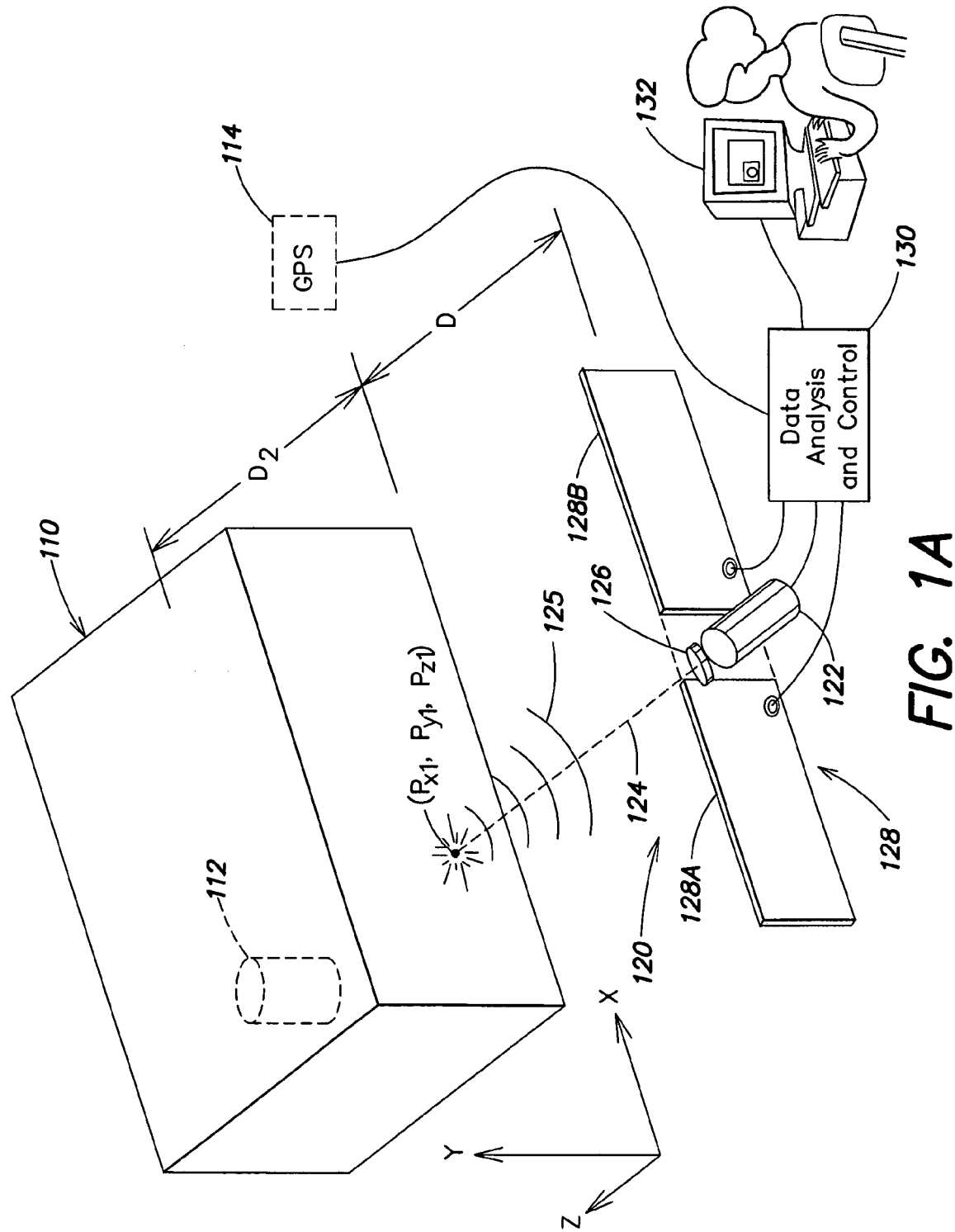
FIG. 1A is a inspection system according to an embodiment of the invention operating at a first point in time.

FIG. 1A illustrates an inspection system according to an embodiment of the invention. In the example pictured in FIG. 1A, a container 110 is being inspected by a security inspection system 120. Security inspection system 120 obtains information about multiple small regions throughout container 110. The exact size of each small region analyzed is not critical to the invention. However, in embodiments of the invention, data is obtained on regions that have a maximum size of about 5 mm (i.e., 5 mm$^3$). The measured value for each of these small regions, when correlated to a physical position of the region within container 110, may serve as the value of a voxel in an image representing container 110.

Security inspection system 120 may include a mechanism to analyze the measured values for each of the voxels to determine whether container 110 contains one or more suspicious regions. A suspicious region may be identified by detecting a group of voxels having values that characterize a contraband item, such as a weapon or explosive. The analysis may be performed automatically within data analysis and control element 130. In some embodiments, data analysis and control element 130 may be implemented by programming a computer or with circuitry designed to perform analysis functions. In yet other embodiments, a combination of programming and circuit elements may be used to implement data analysis and control element 130. Though, it is not necessary that analysis be performed by computer. The measured values of the voxels may be rendered on a display 132 for viewing by a human operator. The human operator may then perform analysis to recognize suspicious regions within the image. Accordingly, the specific mechanism for analyzing an image of container 110 is not a limitation on the invention and any suitable analysis mechanism may be used.

Security inspection system 120 has properties that make it desirable for use in some security applications. As shown in FIG. 1, security inspection system 120 is spaced from the item under inspection by a distance D, which may be relatively large. In some embodiments, D may be on the order of 80 meters. Further, the components of security inspection system 120 may be located on one side of the item other inspection, allowing security inspection system 120 to be implemented in a compact fashion. This combination of properties allows security inspection system to be employed in many settings. For example, a security inspection system may be installed in an area through which containers may pass. Alternatively, security inspection system 120 may be installed on a moving vehicle and brought to a location with containers and other items for inspection. However, the specific setting in which the security inspection system is used is not a limitation on the invention.

Security inspection system 120 is here shown with an x-ray source 122 that emits a pencil beam 124 of radiation. Pencil beam 124 is a narrow beam of collimated rays so that after traveling the distance D the beam has a width comparable to the dimensions of the voxels within container 110 that are to be analyzed. In an embodiment in which voxels are on the order of 5 mm, beam 124 has a width of approximately 5 mm after traveling the distance D. Because beam 124 may spread as it travels distance D, the width of the beam upon leaving the source 122 may be narrower.

As shown, beam 124 is directed at container 110. Beam 124 intersects a region on the surface of container 110, labeled as region ($P_{x1}$, $P_{y1}$, $P_{z1}$). Beam 124 interacts with the material of container 110 at region ($P_{x1}$,$P_{y1}$,$P_{z1}$), resulting in scattered radiation 125. Some portion of scattered radiation 125 propagates back toward a detector panel 128, which in this embodiment is made from sub-panels 128A and 128B. Sub-panels 128A and 128B may contain one or more detector elements sensitive to scattered radiation 125. Accordingly, the output of sub-panels 128A and 128B indicate the magnitude of scattered radiation from container 110. The magnitude of the scattered radiation may depend on one or more properties of the material of container 110 at region ($P_{x1}$, $P_{y1}$, $P_{z1}$) and the magnitude of scattered radiation 125 can be used in forming one voxel of an image of container 110. As shown, the outputs of detector panels 128A and 128B are provided to data analysis and control element 130 processing to form an image.

To form an image of container 110, the region from which scattered radiation emanates is determined. In the example of FIG. 1A, container 110 is positioned in a coordinate system, labeled X, Y, Z. Data analysis and control element 130 controls source 122 and analyzes the output of the detector panel 128 to locate region ($P_{x1}$, $P_{y1}$, $P_{z1}$) in three dimensions. The X and Y coordinates of region ($P_{x1}$, $P_{y1}$, $P_{z1}$) can be readily located by the direction in which beam 124 is pointed if the relative position of security inspection system 120 and container 110 is known. Any suitable mechanism may be used to determine the relative position of an item under inspection and the inspection system. In the embodiment illustrated, a GPS element 114 is placed in close proximity to container 110 and therefore provides position information to data analysis and control element 130. Data analysis and control element 130 may use this position information on container 110 to direct beam 124 to a region on container 110 having a specific X and Y coordinate. However, use of a GPS positioning mechanism is not a requirement of the invention. For example, a relative position may be determined by analyzing radiation scattered from the object. Accordingly, any suitable method for determining the relative position of container 110 and security inspection system 120 may be used.

However, merely pointing beam 124 in a known direction in an X-Y plane does not fully resolve the location of the region ($P_{x1}$,$P_{y1}$,$P_{z1}$) from which scattered radiation 125 is emanating. No information about the Z coordinate of region ($P_{x1}$,$P_{y1}$,$P_{z1}$) is available based on the direction in which beam 124 is pointed. To resolve the location of region ($P_{x1}$, $P_{y1}$,$P_{z1}$), time of flight information may be obtained and used to resolve the Z position of region ($P_{x1}$,$P_{y1}$,$P_{z1}$).

To illustrate how time of flight information resolves the Z position of a region, FIG. 1A illustrates the operation of security inspection system at one instant in time. At the instant shown, beam 124 has propagated just far enough to strike container 110. Accordingly, scattered radiation 125 first emanates from region ($P_{x1}$,$P_{y1}$,$P_{z1}$) after beam 124 has traveled the distance D from source 122 to region ($P_{x1}$,$P_{y1}$, $P_{z1}$). Scattered radiation first reaches detector panel 128 after it has traveled the distance D from region ($P_{x1}$,$P_{y1}$,$P_{z1}$) to detector panel 128. Thus, the first time that scattered radiation is measured is the time it takes for radiation to propagate twice the distance D. This time can be termed the "time of flight."

By measuring the output of detector panel 128 at a time $T_1$ corresponding to the time of flight of radiation over a distance D, data analysis and control system 130 can identify a position in the Z direction region $(P_{x1}, P_{y1}, P_{z1})$ from which the radiation was scattered. Accordingly, the X, Y and Z positions of the region from which the radiation was scattered can be identified.

Once the three-dimensional position of a region from which radiation is scattered has been identified, the measured scatter may be used to form a voxel of an image. Because the characteristics of the scattered radiation, such as its magnitude, can be related to material properties, the scattered radiation can be used to compute the value of a voxel that has an X, Y, Z position that has the same X and Y coordinates as the region at which the radiation is directed and a Z position based on time $T_1$.

Figure 1B:
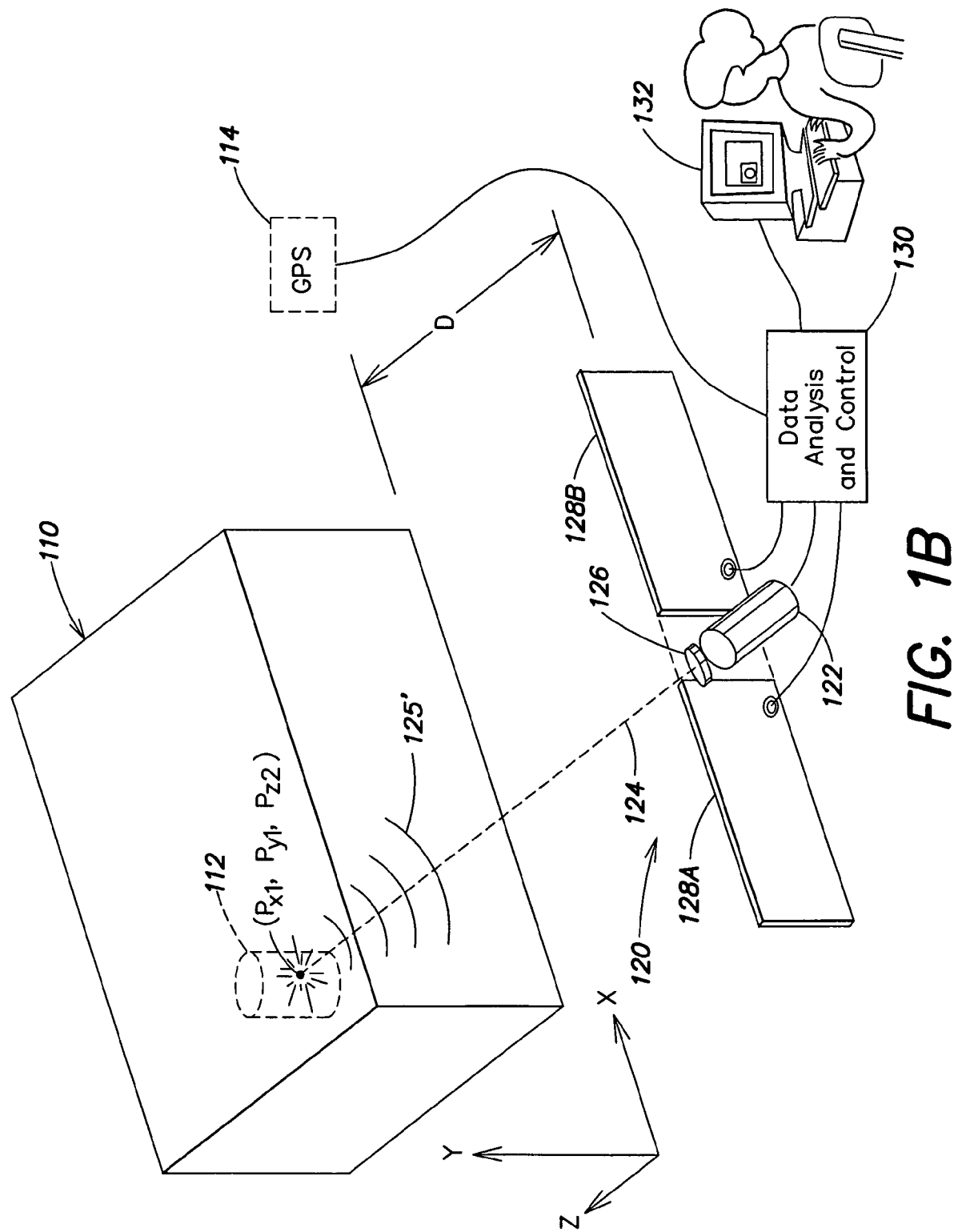
FIG. 1B is a sketch of the inspection system of FIG. 1A operating at a later point in time.

The same approach can be used to measure values that can be used to form other pixels in the image. For example, FIG. 1B shows the system of FIG. 1A operating at a subsequent instant in time. At the time illustrated in FIG. 1B, radiation in beam 124 has propagated through container 110 and has reached object 112. Beam 124 strikes object 112 at region $(P_{x1}, P_{y1}, P_{z2})$, resulting in scattering of scattered radiation 125' from region $(P_{x1}, P_{y1}, P_{z2})$. Because scattering may depend on the material properties of object 112, an image formed of container 110 can reflect the presence of object 112 if scattered radiation 125' can be measured and related to a specific region within container 110.

As with region $(P_{x1}, P_{y1}, P_{z1})$, the X and Y coordinates of region $(P_{x1}, P_{y1}, P_{z2})$ may be determined from the region in an X-Y plane at which beam 124 is pointed. Also, the Z coordinate of region $(P_{x1}, P_{y1}, P_{z2})$ may be determined by time of flight between the region and source 122. In the example of FIG. 1B, the one way distance between source 122 and region $(P_{x1}, P_{y1}, P_{z2})$ is $(D+D_2)$, which results in a time of flight of $T_2$. Thus, by measuring radiation at a time $T_2$ after beam 124 is directed at a container 110, the X, Y and Z position of a voxel corresponding to region $(P_{x1}, P_{y1}, P_{z2})$ may be determined.

To determine values for other voxels in the image, scattered radiation likewise can be measured at other times when beam 124 is pointed at a region with the same X-Y coordinates. Scattered radiation also can be measured when beam 124 is pointed at regions with different X-Y coordinates. In some embodiments, the time of measurement and the X-Y position of the beam is varied in a pattern that results in values being measured for regions representing all of container 110. In this way, all of container 110 may be imaged.

Figure 2:
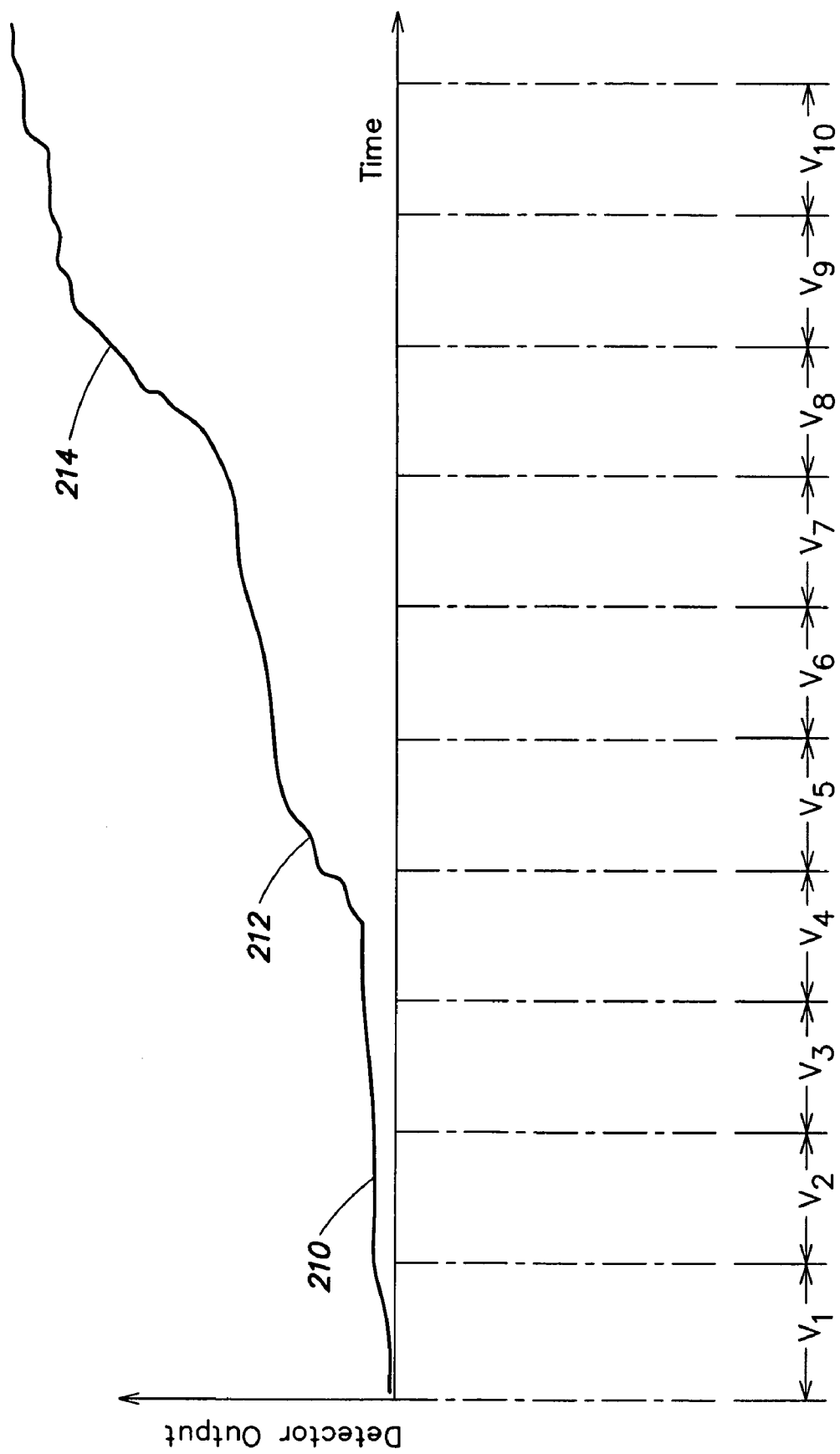
FIG. 2 is a graph showing detector output as a function of time of the system of FIG. 1A.

To make these measurements, in some embodiments, beam 124 may be directed at a region with X-Y coordinates and measurements may then be made of scattered radiation in multiple windows of time. Each window may correspond to a distance from source 122. As an example, FIG. 2 shows the output of detector panel 128 for a period of time after an area in the X-Y plane is illuminated. The start of that period of time may be determined in any suitable way, such as when data analysis and control element 130 steers beam 124 to intersect container 110 or pulses source 122 to create a pulse of radiation in beam 124.

Regardless of how the start of the interval is defined, FIG. 2 shows multiple successive windows, $V_1, V_2 \ldots V_{10}$. During each window, data analysis and control element 130 may measure the output of detector panel 128. Each measurement is therefore correlated to a specific X, Y, Z location within container 110. The measured scatter in each window can therefore be correlated to the value of a voxel with specific X, Y and Z coordinates.

The relationship between the scatter from each region of container 110 and the output of detector panel 128 depicted in FIG. 2 may depend on the time that x-ray beam 124 is directed at a specific X-Y location on container 110. If beam 124 has a duration that is short relative to the time it takes radiation to propagate through container 110, one region of container 110 may be irradiated at a time. In this scenario, because one region is irradiated at a time, the scattered radiation measured during any window can be associated with a single region.

However, if beam 124 has a duration that is long relative to the propagation time through container 110, as the beam propagates through container 110, new regions will be irradiated, while prior regions continue to be irradiated. As a result, scattered radiation measured during any window increases by an amount associated with a newly irradiated region. In this scenario, the rate of change of the scattered radiation measured in any window can be associated with a single region.

For example, FIG. 2 shows that the output of detector panel 128 initially is relatively low, as illustrated by portion 210. Portion 210 indicates that little radiation is scattered as beam 124 propagates through air separating container 110 from security inspection system 120. Measurements taken during windows $V_1$, $V_2$ and $V_3$ indicate that the material in those regions is of a type that does not scatter radiation.

As radiation in beam 124 reaches container 110, radiation begins to scatter from container 110, as reflected by portion 212 in the graph of FIG. 2. Measurements taken during windows $V_5$, $V_6$ and $V_7$ indicate that that the material in those regions is of a type that scatters radiation to a slight degree.

In the example of FIG. 2, as beam 124 propagates into objects within container 110, it encounters material that scatters radiation to a higher degree, as reflected by portion 214 in the graph of FIG. 2. Measurements taken during windows $V_8$ and $V_9$ indicate that that the material in those regions is of a type that scatters radiation to a higher degree than in the regions associated with windows $V_5$, $V_6$ and $V_7$. As demonstrated by this example, measurements taken during different windows of time allow data analysis and control element 130 to determine material properties in regions throughout container 110 and these material properties may be used to form an image of container 110 with values reflecting the properties of the objects within container 110.

FIG. 2 illustrates only ten windows, $V_1, V_2 \ldots V_{10}$, during which the output of the detector panel is measured. This number of windows is shown for simplicity of illustration. Any suitable number of measurement windows may be used.

Moreover, any suitable duration for each measurement window may be used. However, in the embodiment illustrated, the duration of each measurement window determines the longitudinal resolution of voxels (i.e. the size of the voxel in a direction along the x-ray beam). In embodiments in which a resolution of 5 mm is desired, each window may have a duration of 20 psec.

The components of security inspection system 120 may be constructed in any suitable way. For example, detector sub-panels 128A and 128B may be constructed in any suitable way to capture scattered radiation. In the embodiment illustrated, sub-panels 128A and 128B may contain numerous individual detectors. The outputs of the detectors in the detector sub-panels may be combined to produce one value representative of the magnitude of scattered radiation reaching detector panel 128. To increase the sensitivity of security inspection system 120, sub-panels 128A and 128B may be relatively large to increase the amount of scattered radiation captured. In some embodiments, the combined surface area of the detector panels may be in excess of 0.5 m². As a specific example, the combined area of the detector panels may be approximately 1 m².

Any suitable detector panel configuration may be used. Though FIGS. 1A and 1B show two detector sub-panels 128A and 128B, this number of sub-panels is not critical to the invention. A detector panel may be constructed with more than two sub-panels. However, in other embodiments a detector panel may be constructed without sub-panels.

Individual detectors within the detector panel that are sensitive to scattered radiation may be constructed in any suitable fashion. In some embodiments, avalanche photodiodes may be used to form individual detectors in a detector panel. The photodiodes may be formed in any suitable way. For example, avalanche photodiodes may be fabricated directly on substrates, such as silicon, forming sub-panels within the detector panel array. In other embodiments, a scintillating material in combination with a photodiode may be used to form detector elements.

Figure 3:
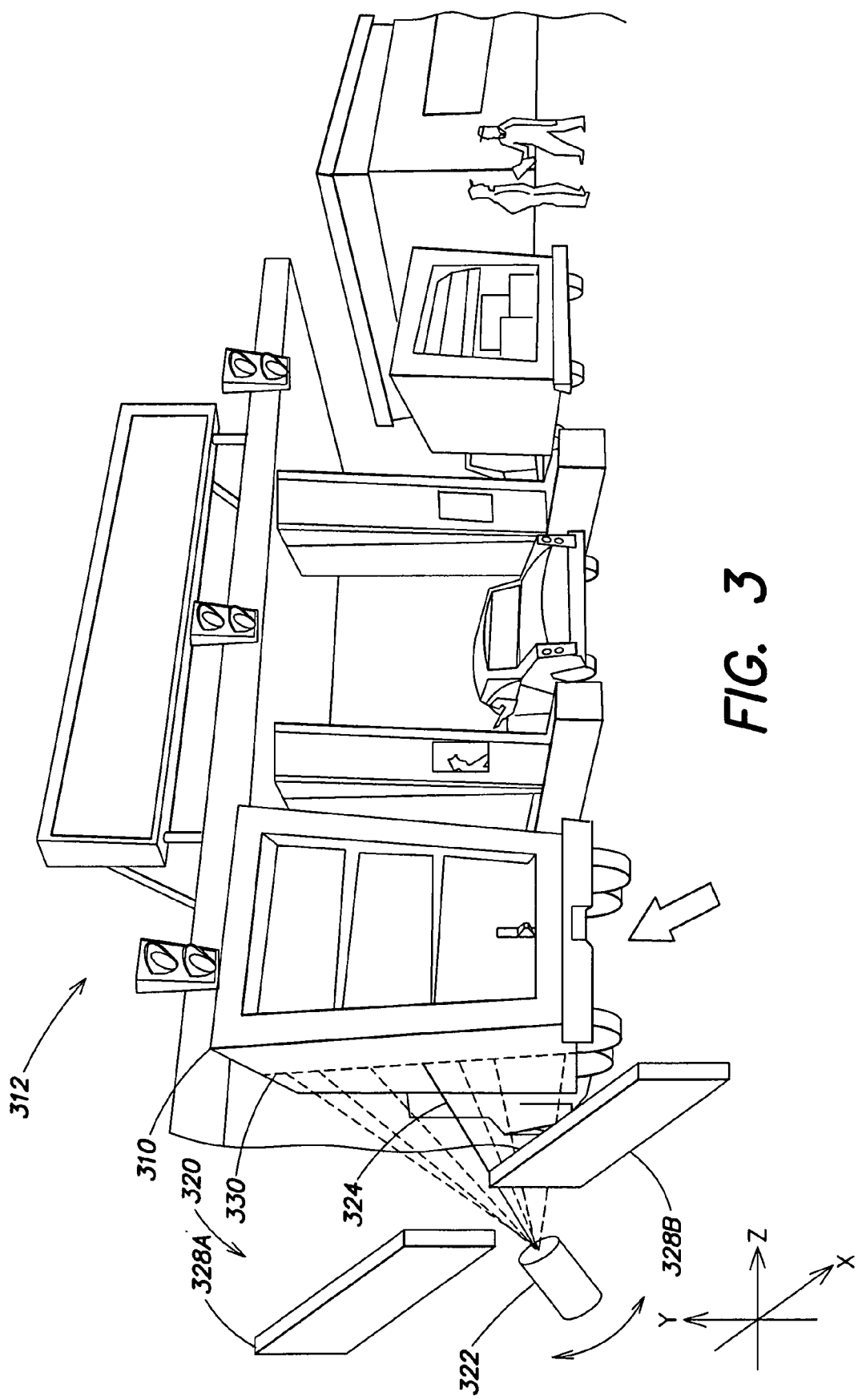
FIG. 3 is a sketch of a security checkpoint incorporating an inspection system according to an embodiment of the invention.

Referring to FIG. 3, further features of a security inspection system according to embodiments of the invention are illustrated. FIG. 3 illustrates a security inspection system applied at a checkpoint 312. In this scenario, items under inspection may be trucks, such as truck 310, or other containers being moved past checkpoint 312. Security inspection system 320 may form images of the items under inspection to detect contraband objects within the item. As described above in connection with FIGS. 1A and 1B, a three-dimensional image of an item under inspection may be formed by directing a narrow beam of radiation at specific regions in a two-dimensional plane and using time of flight to resolve a third dimension. Inspection system 320 includes an x-ray source 322 and detector sub-panels 328A and 328B. In the embodiment of FIG. 3, the x-ray source 322 is operated to successively illuminate areas in a two dimensional plane. For each area in the plane, scattered radiation is detected, and, based on the time of detection of the scattered radiation, the magnitude of the scattered radiation is used to compute the value of a voxel of an image of the item under inspection.

In the embodiment illustrated, the x-ray beam is steered in a raster scan pattern. As shown, source 322 moves back and forth in the Y direction. For each oscillation, beam 324 traces once scan line 330. Relative motion of the security inspection system 320 and item under inspection 310 allows beam 324 to illuminate successive scan lines, each offset from the prior in the X direction. In the embodiment illustrated, relative motion is provided because truck 310 is moving in the X direction. Thus, though source 322 steers beam 324 only in the Y direction, when truck 310 passes security inspection system 320, measurements have been made at multiple points in the XY plane.

Though, it is not necessary for there to be relative motion of security inspection system 320 and item under inspection 310 in order to successively illuminate points in a two dimensional plane. In some embodiments, source 322 may be steered in multiple dimensions to illuminate points throughout the plane.

Figure 4:
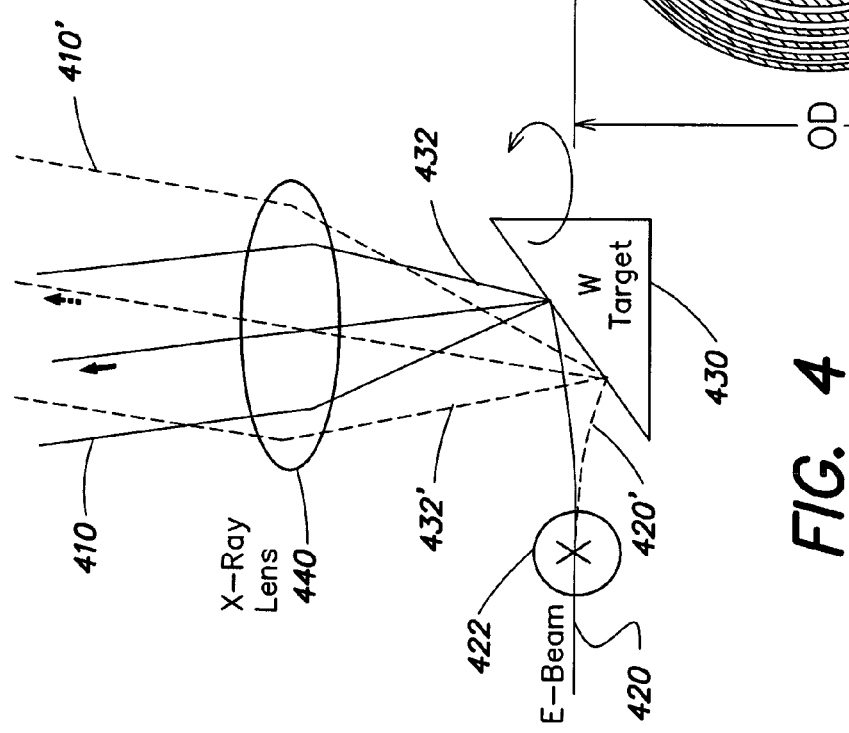
FIG. 4 is a sketch of an x-ray source adapted for steering an x-ray beam according to the embodiment of the invention.

Any suitable mechanism may be used to steer a beam. In some embodiments, mechanical motion of an x-ray source may be used to steer the beam. In other embodiments, the beam may be steered using a magnetic field. FIG. 4 illustrates in schematic form components of an x-ray source that may be steered using a magnetic field. FIG. 4 shows an electron beam 420, which may be generated by a cathode or in any other suitable way. To generate x-rays, electron beam 420 is accelerated towards target 430. In the embodiment illustrated, target 430 is made of tungsten. Regardless of the specific material used to construct target 430, when x-ray beam 420 strikes target 430, radiation 432 is emitted. As emitted, radiation 432 is not focused into a beam. However, an x-ray lens 440 is incorporated into the source, with target 430 positioned at the focal point of lens 440. Accordingly, radiation 432, upon passing through lens 440, is collimated in a beam 410.

To change the direction of beam 410, the point at which electron beam 420 intersects target 430 may be changed. In the embodiment shown, a magnetic field 422 may be applied to electron beam 420. Magnetic field 422 deflects electron beam 420 to position 420'. Accordingly, radiation 432' is generated from a point that is different than the origin of radiation 432. Accordingly, when radiation 432' passes through lens 440, it is focused into a beam 410 in a direction different than beam 410. The amount that beam 410' is steered relative to beam 410 depends on the amount that electron beam 420 is deflected before striking target 430, which in turn depends on the strength of magnetic field 422. Accordingly, by modulating the strength of magnetic field 422, the point of which electron beam 420 strikes target 430 may be changed to steer the beam emitted by the source.

In a system as in the embodiments of FIGS. 1A and 1B, data analysis and control element 130 may control the strength of magnetic field 422. In embodiments in which a beam is steered in two dimension, a magnetic field transverse to magnetic field 422 may be used to steer electron beam 420 in two directions. Alternatively, a beam of radiation may be steered in one dimension by electronically steering an electron beam and in a second direction by mechanical motion of the source. However, the specific mechanism for beam steering is not a limitation of the invention and any suitable mechanism may be used.

The source depicted in FIG. 4, in some embodiments, may carry a current on the order of 200 milliamps. To provide cooling within the source, target 430 may rotate, as illustrated in FIG. 4.

The source depicted in FIG. 4 may be constructed to provide a beam of any suitable energy level. In the embodiments illustrated, the energy of the beam should be sufficiently high to penetrate items under inspection. However, the energy level should be sufficiently low that the beam interacts with material inside the item under inspection to cause sufficient scattering. In some embodiments, the beam may have an energy level of approximately, 40 keV or greater. In some embodiments, the energy in the beam will be approximately 160 keV or less. As a specific example, the beam may have energy of approximately 60 keV.

Figure 5A:
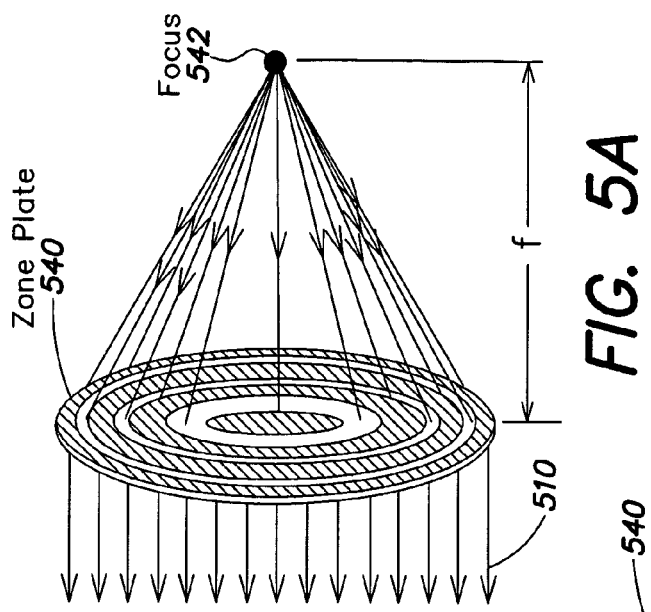
FIGS. 5A and 5B are sketches depicting alternative views of an x-ray lens that may be used in the x-ray source of FIG. 4.
Figure 5B:
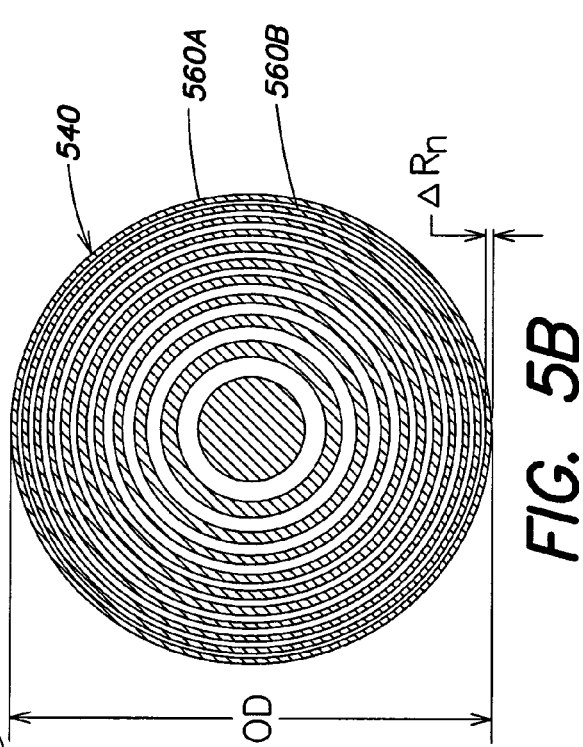

Lens 440 may be implemented in any suitable way. FIGS. 5A and 5B illustrate a lens that may be used in an x-ray source according to embodiments of the invention. FIGS. 5A and 5B show a Fresnel zone plate.

As is known, a Fresnel zone plate focuses radiation emanating from a point 542 into a beam 510 of collimated rays. The focusing results from a pattern of concentric rings spaced with a defined mathematical relation. FIG. 5B illustrates the rings, of which rings 560A and 560B are numbered. A Fresnel zone plate lens may be procured commercially. For example, such a lens may be obtained from Xradia, Inc. of Concord, Calif. Such a zone plate may be constructed with silicon nitride rings coated with gold. Though any suitable construction may be used.

Alternatively, other types of lenses may be used. For example, a compound refractive lens may be used. A compound refractive lens contains multiple refractive structures positioned in the path of x-ray radiation. Though each refractive structure may have a relatively small focusing effect, the combined effect of the multiple structures is to produce a desired level of beam focusing.

Figure 6A:
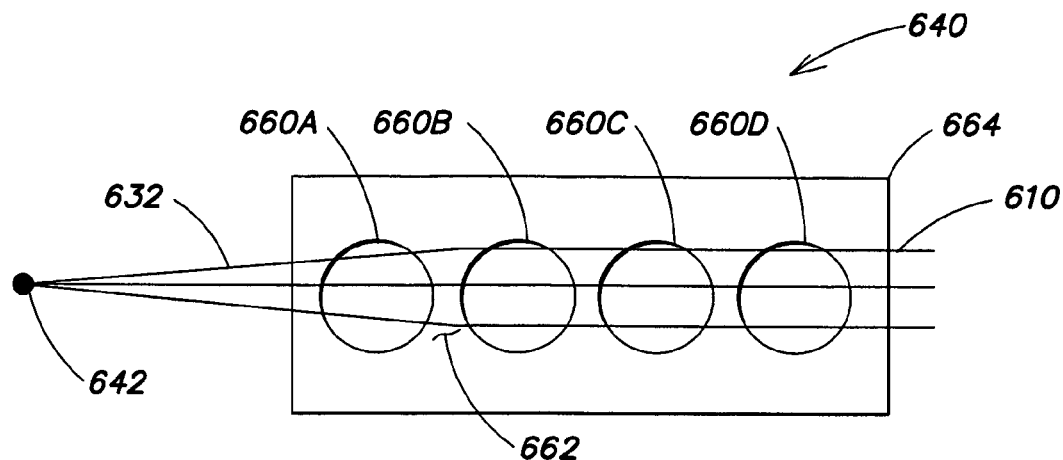
FIGS. 6A and 6B illustrate alternative embodiments of an x-ray lens that may be used in the apparatus of FIG. 4.

FIG. 6A illustrates a compound refractive lens 640 that may be used in an x-ray source according to embodiments of the invention. Compound refractive lens 640 may be constructed by forming a series of holes in a block of material 664. In the embodiment of FIG. 6A, holes 660A, 660B, 660C and 660D are shown. However, any number of holes providing a suitable level of focusing may be used. FIG. 6A illustrates that material between the holes forms regions shaped like parabolic lenses. For example, region 662 between holes 660A and 660B forms one element of the compound lens. Radiation 632 emanating from point 642 may be refracted slightly as it passes through each of the lens elements between the holes. Though the effect at each hole is relative small, the net effect is to focus radiation 632 into a beam 610 of collimated rays.

Figure 6B:
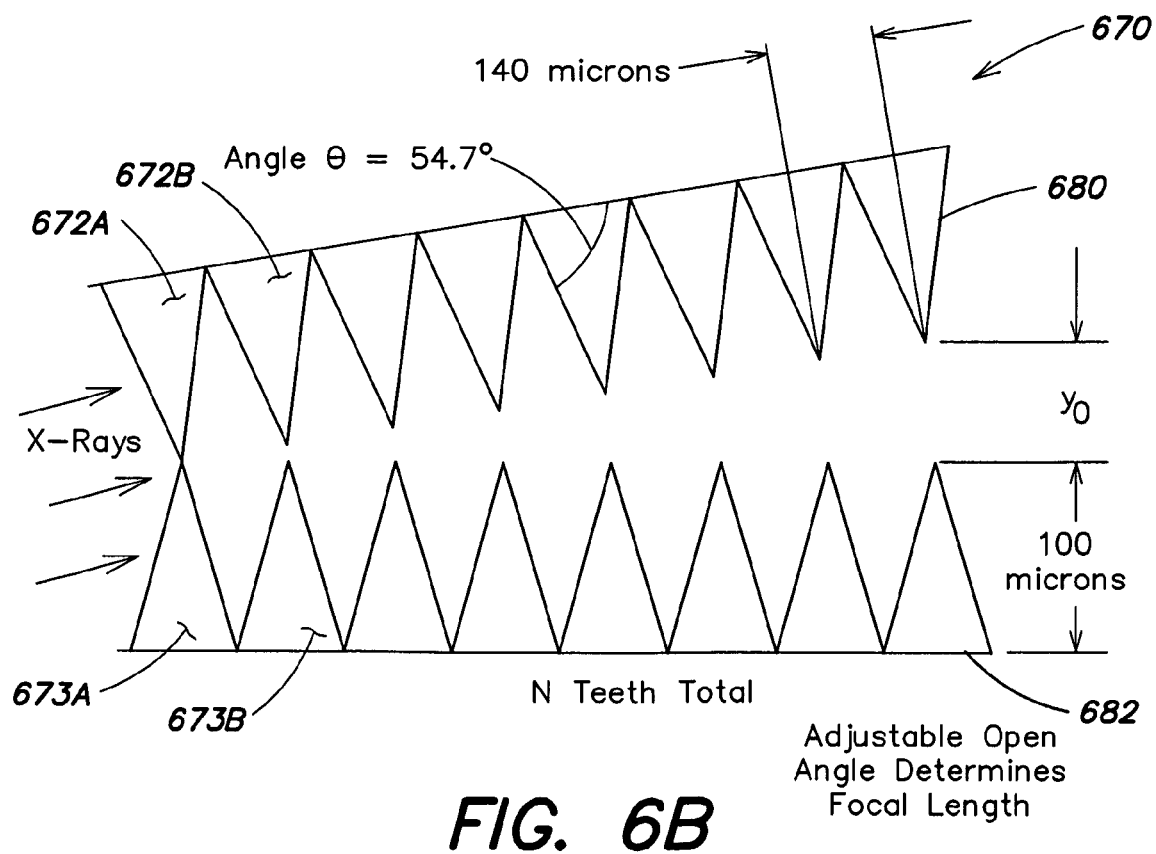

FIG. 6B shows an alternative embodiment of a compound refractive lens. In the embodiment illustrated, compound refractive lens 670 has an upper wall 680 and a lower wall 682, forming a channel between them. Each of the walls 680 and 682 has serrations. In the embodiment illustrated serrations 672A and 672B are numbered in upper wall 680. Serrations 673A and 673B are numbered in lower wall 682. Though eight serrations are shown in each of upper wall 680 and lower wall 682 any number of serrations providing a suitable level of focusing may be used.

A compound refractive lens may be made of any suitable material that causes refraction of x-ray radiation. Examples of suitable material include beryllium, lithium and aluminum. Though in some embodiments, silicon, plastic or other materials may also be used.

Figure 7:
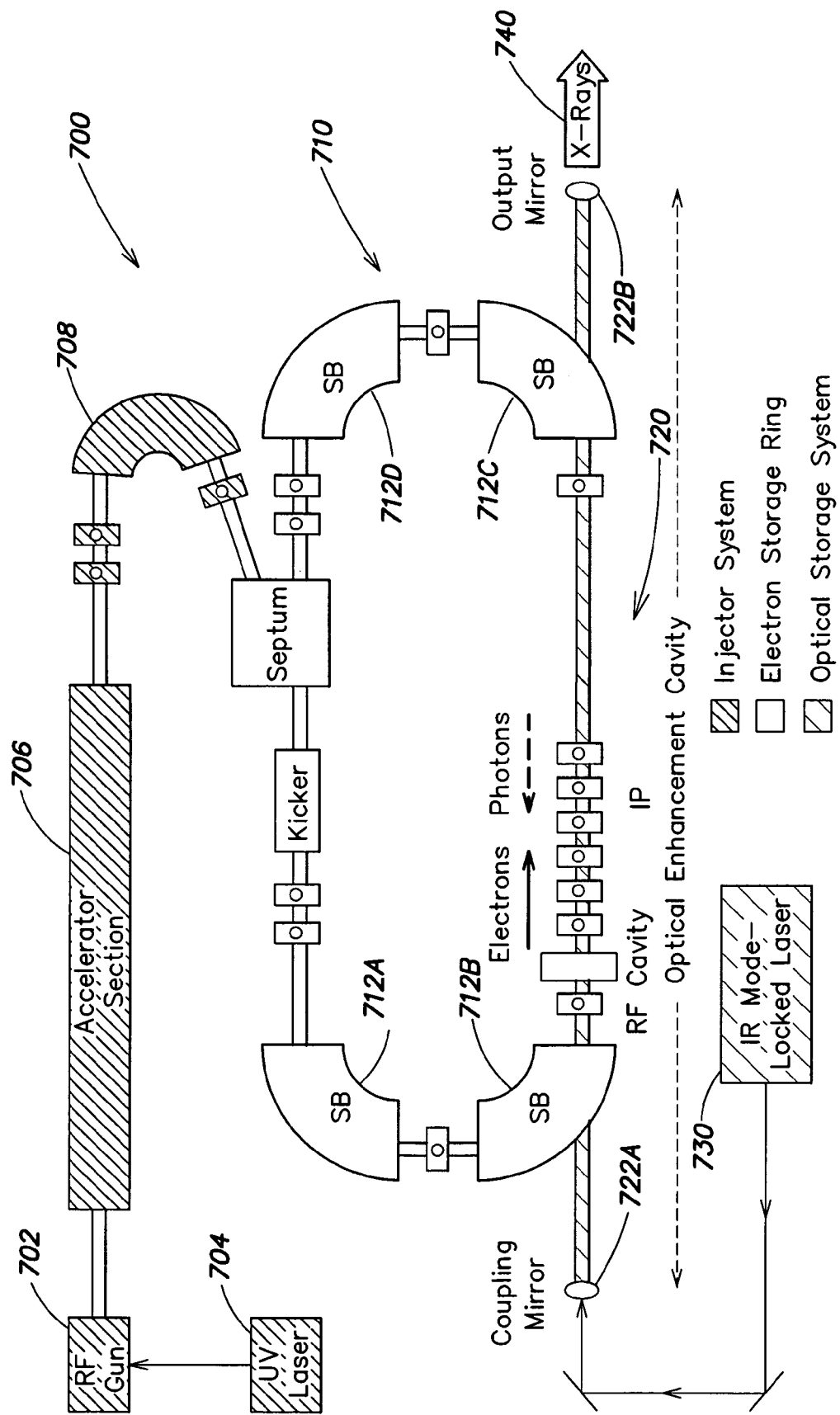
FIG. 7 is a sketch of an x-ray source according to an alternative embodiment of the invention.

FIG. 4 illustrates an embodiment of an x-ray source that may be used to generate a narrow x-ray beam. As a specific example, an x-ray beam with a width of 5 mm at a range of 80 m may be formed. FIG. 7 provides an example of an alternative embodiment of an x-ray source. The x-ray source depicted in FIG. 7 generates x-rays by the interaction of electrons and photons. X-ray source 700 generates packets of electrons that interact with packets of photons. The packets of electrons are generated in RF gun 702, which is controlled by UV laser 704. The electron packets are accelerated through accelerator section 706. A magnet 708 deflects the packets of electrons into an electron storage ring 710.

Electron storage ring 710 is formed by multiple magnets, such as magnets 712A, 712B, 712C and 712D. Superimposed in one segment of electron storage ring 710 is an optical enhancement cavity. The optical enhancement cavity 720 is formed between mirrors 722A and 722B. IR mode-locked laser 730 may inject light through mirror 722A into optical enhancement cavity 720 and photons from that laser may propagate back and forth between mirrors 722A and 722B.

As electron packets travel around electron storage ring 710, they will interact with photons within the optical enhancement cavity 720, emitting a narrow x-ray beam 740. Mechanical positioning of x-ray source 700 may direct beam 740 for scanning an item under inspection. However, any suitable means may be used to steer x-ray beam 740.

Additional details of x-ray source 700 may be found in a paper entitled "A Compact Light Source: Design and Technical Feasibility Study of a Laser-Electron Storage Ring X-Ray Source," by Roderick J. Loewen of the Stanford Linear Accelerator Center of Stanford University, Stanford, Calif., published as Report SLAC—Report—632, June 2003 and submitted to the Department of Physics of Stanford University as a dissertation in partial fulfillment of the requirements for the degree of Doctor of Philosophy. That report is hereby incorporated by reference in its entirety.

Figure 8:
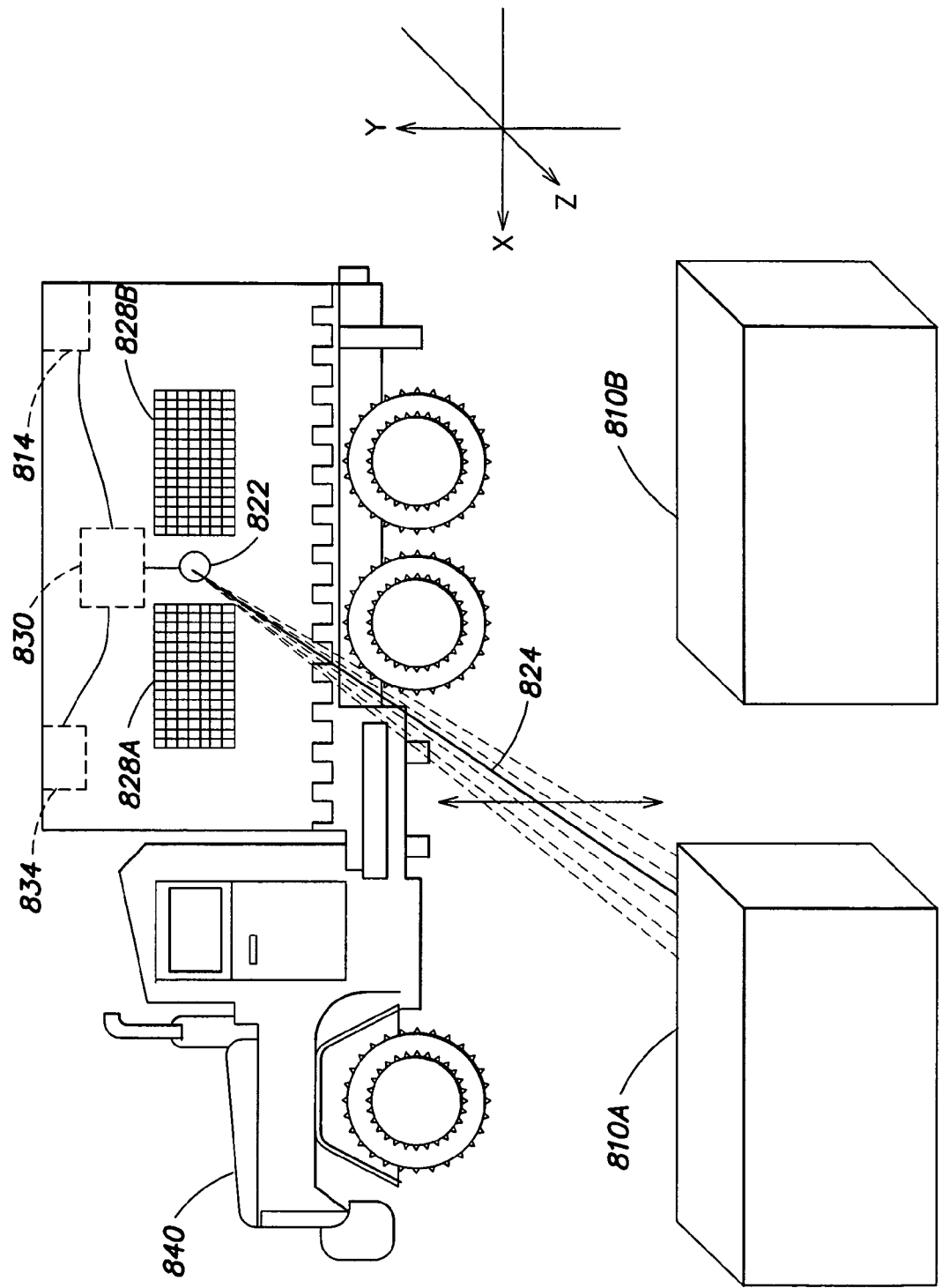
FIG. 8 is sketch of an imaging system incorporated into a vehicle according to the embodiment of the invention.

Regardless of the specific manner in which an x-ray beam is generated and steered, an imaging system according to embodiments of the invention may be incorporated into security inspection systems of multiple types. FIG. 8 shows as a further example a security inspection system that is mounted on a vehicle, such as a truck 840.

The security inspection system includes an x-ray source 822 producing a narrow beam of radiation. A detector panel may also be mounted on truck 840. In the embodiment illustrated, a detector panel is created with two detector sub-panels 828A and 828B. Each detector sub-panel includes multiple detector elements that can sense radiation scattered from an item under inspection when illuminated by a beam 824 emitted by source 822. However, detector panels may be constructed in any suitable way. Because, in the described embodiment, the outputs of the individual detectors in sub-panels 828A and 828B are combined, the number of detector elements within sub-panels 828A and 828B is not critical to the invention. For example, a panel formed from a single detector element may be suitable for us in embodiments of the invention.

In operation, beam 824 is scanned over items under inspection, such as containers 810A and 810B. In the embodiment illustrated, scanning results from motion of beam 824 in two directions, denoted X and Y. In the specific embodiment of FIG. 8, motion in the X direction may result from motion of truck 840. Motion in the Y direction may result from steering beam 824 in the Y direction. However, any suitable mechanism may be used for steering beam 824. In the embodiment illustrated, motion of beam 824 in the Y direction is coordinated with the motion in the X direction so that beam 824 traces out a raster scan pattern on items under inspection. However, any pattern that results in a suitable number of points on an item under inspection being illuminated may be used.

To control scanning of source 822, a data analysis and control element 830 may be included in truck 840. As with data analysis and control element 130 (FIG. 1A), data analysis and control element 830 may control the x-ray source and may also capture and analyze the outputs of the detector panel. In addition, data analysis and control element 830 may receive inputs from sensors on truck 840 to use in steering beam 824 and coordinating measurements from detector array panels 828A and 828B. In the embodiment illustrated, data analysis and control element 830 may receive input from a navigation system that defines the position and speed of vehicle 840. In the embodiment illustrated, truck 840 is shown to be equipped with a global positioning system 814 that provides input to data analysis and control element 830. However, information concerning the location and motion of truck 840 may be obtained in any suitable way.

Additionally, data analysis and control element 830 may steer beam 824 to compensate for vibration or other high frequency motion of vehicle 840. Accordingly, FIG. 8 shows a vibration sensor 834 providing input to data analysis and control element 830. Data analysis and control element 830 may use the output of vibration sensor 834 to steer beam 824 to compensate for vibration or other unwanted motion of truck 840.

In operation, truck 840 moves in the direction labeled X. For example, truck 840 may move at 15 to 20 m/sec. Data analysis and control element 830 steers beam 824 in a pattern across an item under inspection 810A to successively illuminate points on the surface of item 810A. At each point, a pulse of radiation is delivered in beam 824. The output of the detector panel is measured at successive intervals following delivery of the pulse. In the embodiment illustrated, the intervals at which the output of the detector panel is measured are separated in time by a sufficiently small amount to provide a required resolution in the Z direction. In some embodiments, measurement windows for the outputs of the detector panels are between approximately 10 picoseconds and approximately 80 picoseconds. As a specific example, the measurement windows may be 20 picoseconds in some embodiments. Though in other embodiments where lower resolution is suitable, the measurement window may be 30 picoseconds.

The measurements taken in each window are used to determine a value for a voxel in an image of the item under inspection. This image may then be analyzed to detect contraband within the item.

Having thus described several aspects of at least one embodiment of this invention, it is to be appreciated that various alterations, modifications, and improvements will readily occur to those skilled in the art.

For example, it is not a requirement of the invention that the imaging system be used to implement a security inspection system. The imaging system may be used to analyze buildings, bridges and other structures for faults that could impact the integrity of those structures.

In some embodiments, further information on an item under inspection may be obtained by measuring a difference in energy level between the incident radiation in beam 124 and scattered radiation, such as scattered radiation 125 and 125' (FIG. 1A or FIG. 1B). In such embodiments, it may be desirable to include a filter 126 (FIG. 1A or FIG. 1B) in the path of beam 124. Filter 126 may make beam 124 relatively monochromatic, allowing the difference between the energy in the incident and scattered radiation to be detected. If energy shifts are detected and analyzed, detector array panels 128A and 128B may be sensitive to radiation of different energies.

Further, detector panels are shown to be immediately adjacent an x-ray source. In embodiments in which radiation scatters in multiple directions, detector panels may be positioned in any location where a suitable level of scatter may be detected.

Also, embodiments of the invention are described in which regions from which radiation scatters are described in a Cartesian coordinate system. Such a description is provided for simplicity of illustration and may be appropriate for embodiments in which a source translates in the X-Y plane so that the beam is orthogonal to the X-Y plane. Use of a Cartesian coordinate system may also represent an acceptable approximation when the separation between an item under inspection and a security inspection system is large relative to the width of the item under inspection. However, in embodiments in which the beam is steered without translating the source, regions may be located more accurately using a coordinate system with a direction of the beam defining one dimension. Of course, even if such a coordinate system is used, regions for which measurements are made can be translated to a Cartesian coordinate system, or any other suitable coordinate system, for analysis.

Also examples of x-ray sources were provided. As another example, a beam may be formed with a synchrotron.

Such alterations, modifications, and improvements are intended to be part of this disclosure, and are intended to be within the spirit and scope of the invention. Accordingly, the foregoing description and drawings are by way of example only.

The above-described embodiments of the present invention can be implemented in any of numerous ways. For example, embodiments may be implemented using hardware, software or a combination thereof. When implemented in software, the software code can be executed on any suitable processor or collection of processors, whether provided in a single computer or distributed among multiple computers.

Further, it should be appreciated that a computer may be embodied in any of a number of forms, such as a rack-mounted computer, a desktop computer, a laptop computer, or a tablet computer. Additionally, a computer may be embedded in a device not generally regarded as a computer but with suitable processing capabilities.

Also, a computer may have one or more input and output devices. These devices can be used, among other things, to present a user interface. Examples of output devices that can be used to provide a user interface include printers or display screens for visual presentation of output and speakers or other sound generating devices for audible presentation of output. Examples of input devices that can be used for a user interface include keyboards, and pointing devices, such as mice, touch pads, and digitizing tablets. As another example, a computer may receive input information through speech recognition or in other audible format.

Such computers may be interconnected by one or more networks in any suitable form, including as a local area network or a wide area network, such as an enterprise network or the Internet. Such networks may be based on any suitable technology and may operate according to any suitable protocol and may include wireless networks, wired networks or fiber optic networks.

Also, the various methods or processes outlined herein may be coded as software that is executable on one or more processors that employ any one of a variety of operating systems or platforms. Additionally, such software may be written using any of a number of suitable programming languages and/or conventional programming or scripting tools, and also may be compiled as executable machine language code or intermediate code that is executed on a framework or virtual machine.

In this respect, the invention may be embodied as a computer readable medium (or multiple computer readable media) (e.g., a computer memory, one or more floppy discs, compact discs, optical discs, magnetic tapes, flash memories, circuit configurations in Field Programmable Gate Arrays or other semiconductor devices, etc.) encoded with one or more programs that, when executed on one or more computers or other processors, perform methods that implement the various embodiments of the invention discussed above. The computer readable medium or media can be transportable, such that the program or programs stored thereon can be loaded onto one or more different computers or other processors to implement various aspects of the present invention as discussed above.

Computer-executable instructions may be in many forms, such as program modules, executed by one or more computers or other devices. Generally, program modules include routines, programs, objects, components, data structures, etc. that perform particular tasks or implement particular abstract data types. Typically the functionality of the program modules may be combined or distributed as desired in various embodiments.

Various aspects of the present invention may be used alone, in combination, or in a variety of arrangements not specifically discussed in the embodiments described in the foregoing and is therefore not limited in its application to the details and arrangement of components set forth in the foregoing description or illustrated in the drawings. For example, aspects described in one embodiment may be combined in any manner with aspects described in other embodiments.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

What is claimed as new and desired to be protected by Letters Patent is:

1. A method of imaging an item, comprising:
   a) redirecting, with at least one focusing element, divergent x-rays to form a collimated x-ray beam;
   b) scanning the x-ray beam over the item;
   c) measuring the intensity and scattering time of radiation scattered from the item, wherein measuring the scattering time comprises measuring an arrival time of the scattered radiation relative to a time at which the beam is emitted by a source; and
   d) forming an image of the item based at least in part on the measured intensity and scattering time.

2. The method of claim 1, wherein forming an image comprises forming a three-dimensional image.

3. The method of claim 2, wherein:
   scanning comprises successively directing the x-ray beam at each of a plurality of irradiated areas; and
   measuring comprises detecting radiation scattered while the x-ray beam is focused at each of the plurality of irradiated areas.

4. The method of claim 1, further comprising:
   steering an electron beam over a target to generate the divergent x-rays.

5. The method of claim 4, wherein steering the electron beam comprises varying the strength of a magnetic field.

6. The method of claim 1, further comprising:
   analyzing the image to determine whether the item contains an explosive.

7. The method of claim 1, wherein the at least one focusing element comprises a lens.

8. The method of claim 7, wherein the lens is a refractive compound lens.

9. The method of claim 7, further comprising:
   filtering the divergent x-rays.

10. The method of claim 1, wherein the at least one focusing element comprises a zone plate.

11. The method of claim 1, wherein scanning the beam over the item comprises moving the item relative to an x-ray source.

12. The method of claim 1, wherein the item comprises a vehicle and scanning the beam comprises moving the vehicle relative to the source.

13. The method of claim 1, wherein the item is located in excess of 50 meters from the source.

14. A method of imaging an item, comprising:
   a) redirecting, with at least one focusing element, divergent x-rays to form a collimated x-ray pencil beam;
   b) scanning the pencil beam over the item, the scanning comprising successively directing the pencil beam at each of a plurality of irradiated areas;
   c) measuring the intensity and scattering time of radiation scattered from the item, the measuring comprising detecting radiation scattered while the pencil beam is focused at each of the plurality of irradiated areas; and
   d) forming a three-dimensional image of the item based at least in part on the measured intensity and scattering time, the forming comprising assigning values based on an intensity of the radiation scattered from the item to a three-dimensional array of voxels, each voxel having a position in a first dimension and a second dimension based on a position in a first dimension and a second dimension of an irradiated area and a position in a third dimension proportional to an arrival time measured for the irradiated area.

15. The method of claim 14, wherein the collimated x-ray beam is emitted by a source, and the item is located in excess of 50 meters from the source.

16. An inspection system, comprising:
   a) a steerable source with at least one focusing element, the source being adapted to emit a collimated beam of radiation toward an illumination area, the collimated beam being shaped to have a width less than 10 mm at a distance of 70 meters;
   b) a detector panel positioned to receive radiation from the direction of the illumination area; and
   c) a data analysis system, adapted to form an image of an item proximate the illumination area, the image comprising a plurality of regions, each region having a value based on the magnitude of an output of the detector panel at a detection time and a difference between (i) a time at which the collimated beam of radiation is emitted toward the illumination area and (ii) the detection time.

17. The inspection system of claim 16, wherein the detector array has an area greater than 0.5 square meters.

18. The inspection system of claim 17, wherein the detector array has an area greater than 1 square meter.

19. The inspection system of claim 17, wherein the detector array comprises a plurality of avalanche photodiodes.

20. The inspection system of claim 16, wherein the x-ray source and the detector array are mounted to a vehicle.

21. The inspection system of claim 17, wherein the at least one focusing element comprises a Fresnel zone plate.

22. The inspection system of claim 17, wherein the at least one focusing element comprises a compound refractive lens.

23. The inspection system of claim 22, wherein the compound refractive lens comprises an aperture bounded by at least one serrated wall.

24. The inspection system of claim 23, wherein the at least one serrated wall is formed of beryllium or lithium.

25. The inspection system of claim 22, wherein the compound refractive lens comprises a member having a plurality of holes therein, the holes forming an x-ray path.

26. The inspection system of claim 16, wherein the item is located in excess of 50 meters from the source.

* * * * *